United States Patent [19]

Avery, Jr.

[11] 4,183,684
[45] Jan. 15, 1980

[54] FLUID DISPENSING UNIT

[75] Inventor: Carl F. Avery, Jr., Roscoe, Ill.

[73] Assignee: Marion Health & Safety, Inc., Rockford, Ill.

[21] Appl. No.: 855,678

[22] Filed: Nov. 29, 1977

[51] Int. Cl.² ............................................. A61M 35/00
[52] U.S. Cl. ..................................... 401/133; 128/269; 401/139
[58] Field of Search .............................. 401/132–134, 401/135, 139, 196; 128/269, 272; 206/219

[56] References Cited

U.S. PATENT DOCUMENTS

| | | | |
|---|---|---|---|
| 1,287,487 | 12/1918 | Smith | 401/196 |
| 2,371,667 | 3/1945 | Arena et al. | 401/132 X |
| 3,386,793 | 6/1968 | Stanton | 401/132 |
| 3,403,961 | 10/1968 | Gazzani | 401/202 |
| 3,466,131 | 9/1969 | Arcudi | 401/132 |
| 3,636,922 | 1/1972 | Ketner | 401/132 X |
| 3,768,916 | 10/1973 | Avery | 401/132 |
| 3,891,331 | 6/1975 | Avery | 401/132 |

FOREIGN PATENT DOCUMENTS 1016053  1/1966  United Kingdom .................... 401/132

*Primary Examiner*—Paul T. Sewell
*Attorney, Agent, or Firm*—Watson, Leavenworth, Kelton & Taggart

[57] ABSTRACT

A fluid dispensing unit having a housing in which is carried a fluid-containing ampoule and a porous pad secured to the underside of the housing has its structural integrity enhanced by a central planar depression formation in the housing top wall to thereby facilitate rupturing the ampoule without hazard of broken glass puncturing the housing walls. An improved porous pad structure also is provided.

9 Claims, 6 Drawing Figures

FLUID DISPENSING UNIT

BACKGROUND OF THE INVENTION

The present invention relates to improvements in a fluid dispensing unit of the type described in abandoned application Ser. No. 479,353 filed June 14, 1974.

The said abandoned application discloses a fluid dispensing unit which can be used for containing and dispensing various fluids and liquids such as medicaments, cleansing agents, cosmetic preparations, polishes and a generally wide range of liquidous materials. The unit disclosed in said application includes a body made of flexible material which has a top wall, side walls, end walls and a flange extending around the base of the end and side walls to define an opening at the bottom of the body, there being connected to the flange and in covering position over the opening in the body, a porous or sponge-like material layer which can be secured to the body in various manners. Carried within the body is an ampoule containing the fluid to be dispensed through the porous body. To release the fluid from the ampoule, a squeezing force is applied to the body side walls so as to effect fracturing of the ampoule and the fluid is thereby released into and through the porous member for the intended use. While such device is satisfactory for its intended purpose, it has a disadvantage that when the side walls are squeezed together to fracture the ampoule, and due to the particular configuration and construction of the top wall, the fingers of the user do not have a fulcrumming surface which can be employed to optimally control the squeezing force applied, so that on occasion and if too much squeezing force is applied to the side walls, particles of glass from the broken ampoule can penetrate the side wall structure and cause injury to the users' fingers.

Dispensing units of the general type with which the said abandoned application and with which the present invention is concerned, are known in the prior art. Pertinent in this respect are the United States patents and foreign patent to be discussed next.

U.S. Pat. No. 3,403,961 describes a dispensing device which includes a body part 10 that receives and holds a phial F containing liquid to be dispensed. The body further includes a skirted lower portion in which is received a sponge applicator with the two body portions having an opening 18 through which fluid outflow from the phial is communicated to the sponge. The device is intended to be reusable but it is not used with a frangible phial, that is one that is fractured to release fluid therefrom. Accordingly, no consideration is given or suggested to the need for special constructional features to prevent penetration of any broken particles from a phial through the handle part of the body.

The Staunton U.S. Pat. No. 3,386,793 discloses an applicator for liquids, paste and like materials which has a flexible compressible housing from which liquid is dispensed through a sponge secured to the bottom of the housing. There is no frangible ampoule or phial associated with the device and there is no need to specially strengthen the housing for that reason. The fluid containing housing, however, is constructed such that the walls can be squeezed together to a considerable degree so that if it were used with a frangible ampoule, there is strong likelihood that particles of the phial could penetrate the wall structure to the detriment of the user.

U.S. Pat. No. 2,371,667 discloses the covering of frangible fluid-containing ampoules with several layers of absorbent material applied over the ampoules in the form of inner and outer hoses of absorbent material. No special consideration or provision is made to prevent penetration of the absorbent layers by any jagged or sharp edged particles of the ampoule structure following the rupture of the same.

U.S. Pat. No. 3,636,922 discloses various embodiments of fluid applicators in which a readily rupturable or frangible fluid-containing unit is housed within an absorbent or sponge-like mass. The shapes of devices disclosed are, however, in no way similar to those set forth in the abovementioned abandoned patent application.

U.S. Pat. No. 3,466,131 describes a dispensing applicator package in which a frangible spherical shaped fluid container is housed within a correspondingly spherical shaped body chamber 10. The side walls of the body chamber are squeezed together to break the fluid container and permit release of fluid to the sponge element 22. The top wall of the housing does not have any strengthening feature as would insure prevention of penetration by particles of the broken ampoule through the side walls. Since the top wall is joined to the side wall at rounded corner juncture, it is believed that the top wall would bulge upwardly when finger squeezing pressure was applied to the device thereby lessening the degree of control the user would have in applying such pressure and increasing the possibility of excessive pressure causing puncture of the wall by particles of the broken ampoule.

U.S. Pat. No. 3,768,916 discloses a scrubbing unit in which a frangible ampoule is received in a slot formed in a sponge member and a rigid cap fitted over the ampoule and slot with the sides of the cap being drawn together to compress upper portions of the sponge to facilitate directing outflow of fluid from the broken ampoule and also to prevent particles of the broken ampoule from passing through the sponge to the user's fingers. However, the device does not have a body or housing structure comparable to that described in the above-identified abandoned application and to which the present invention pertains.

British Pat. No. 1,016,053 discloses a liquid dispenser in which a frangible ampoule is housed within a cylindrical sleeve closed at one end and the other end of which is fitted an applicator device 4. No special strengthening feature is embodied in this device to prevent penetration of the sleeve by glass fragments from the ampoule.

SUMMARY OF THE INVENTION

The present invention is concerned with improvements in a fluid dispensing unit of the type described in abandoned application Ser. No. 479,353. In accordance with the present invention, the dispensing unit which comprises a housing having top, side and end walls, and an open bottom with there being a flange extending in an encircling course around the bottom opening and formed integrally with the side and end walls of the housing, with the housing having a porous pad member connected thereto in covering position over the said opening. The porous pad member can be connected to the underside of the flange in various ways as by bonded connection wherein solvent or other bonding means can be employed, or the housing and porous pad member can be of heat sealably compatible materials and the pad member heat sealed to the flange. Disposed within the housing are pairs of indentations formed in the side walls and which define a cradle for receiving an elongated frangible ampoule containing a fluid to be dispensed to and through the porous pad member when the ampoule is fractured by digitally applied squeezing action applied to the side walls of the housing. As provided by the present invention, the structure of the housing is strengthened to enhance its rigidity particularly in the region thereof where the digitally applied pressure is applied when breaking the ampoule. For this purpose the housing top wall is provided with a central planar segment that is stepped down relative to terminal segments of the top wall and which central planar segment merges with substantially right angularly disposed planar portions of the housing side walls. This arrangement thus defines an inverted housing channel structure of enhanced rigidity which embraces the ampoule. Thus, when digital pressure is applied to fracture the ampoule, the user's fingers find that the juncture of the central segment of the top wall and the right angularly disposed portions of the side wall are at sharp corner juncture to constitute fulcrum points so that the squeezing together of the side walls is limited to a pivoting of each toward the other about the respective fulcrum points. This results in the user having better control over the movement of the fingers so that when sufficient pressure has been applied to fracture the ampoule, the fingers readily can be withdrawn outwardly to obviate application of such excessive pressure as could result in the side walls being pressed into the broken fragments of the ampoule with possible consequent injury to the user's fingers. In prior devices and particularly that described in the above-identified abandoned application, the housing structure does not possess such rigidity as allows the user to optimally control squeezing action since the side walls do not pivot toward each other but rather displace inwardly in a movement as includes deformation or upward bulging of the top wall itself.

The central planar segment of the top wall is arranged in the housing such that it extends parallel with the flange at the bottom of the housing which flange in turn is disposed in a single plane, and furthermore, the central planar segment has merging transition with the top wall terminal segments along an upwardly curving course all of which lends to enhancing the structural character of the housing in such region.

In accordance with the invention, the porous pad member can be a plural ply element including a guazelike sheet layer and a sponge layer of a reticulated open-cell foam material bonded or laminated to the sheet layer with the sheet layer being located immediate or adjacent the flange. In securing the porous pad member to the underside of the housing flange, the same can, as mentioned above, be bonded in a full encircling course or it can be heat sealed to the flange.

A further improvement of the present invention provides that the porous pad member be provided along the longitudinal margins thereof and at spaced locations therealong, with a plurality of dimples which conveniently can be fashioned by effecting a heat seal of the porous pad member to the flange at spaced locations. The dimples are arranged at each margin in pairing with like dimples at the other margin so that between each pair of dimples and an adjacent pair, there is formed in the pad member a discrete pad segment which arrangement facilitates the saturation of the pad member with fluid following the rupturing of the ampoule as well as providing plural scrubbing segments to enhance the scrubbing action with which the pad member can be employed.

The objects of the invention and its advantages will be made more fully apparent from a consideration of the preferred embodiments to be given hereinafter.

BRIEF DESCRIPTION OF THE DRAWINGS

The invention will appear more clearly from a detailed description of the preferred embodiments to be given in the following description taken together with the accompanying drawings.

Throughout the description like reference numerals are used to denote like parts in the drawings.

DESCRIPTION OF THE PREFERRED EMBODIMENTS

The present invention is concerned with improvements in fluid dispensing units and is characterized by particular improvements in the dispensing unit described in abandoned application Ser. No. 479,353. In more particularlity it is concerned with enhancing the structural character of the housing component of the dispensing unit to insure that upon fracturing the frangible fluid filled ampoule disposed within the housing, that broken particles of glass or like material of the fractured ampoule do not penetrate the side walls of the housing; and additionally, improvement is directed to effecting a dimpling of the porous pad member at the underside of the housing along the longitudinal margins thereof to form a plurality of pad or sponge segments therein to enhance saturation of the porous pad member upon rupturing of the ampoule and to provide plural sponge or pad segments as enhance the scrubbing or cleansing character of the device.

Figure 1:
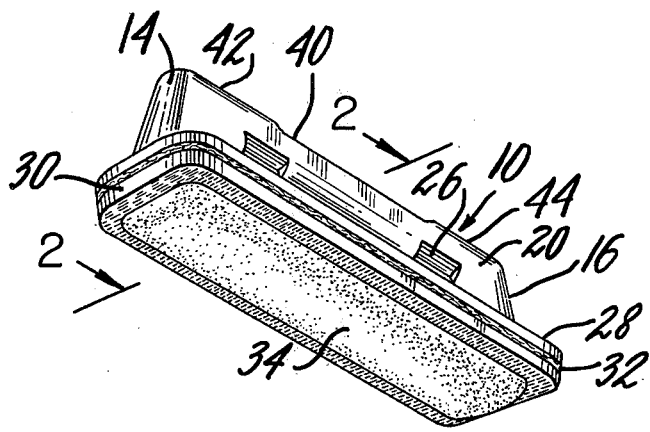
FIG. 1 is a perspective view of one embodiment of the fluid dispensing unit of the present invention wherein the porous pad member is connected to the housing flange by heat sealing extending in an encircling course in correspondence to the course of the flange.
Figure 2:
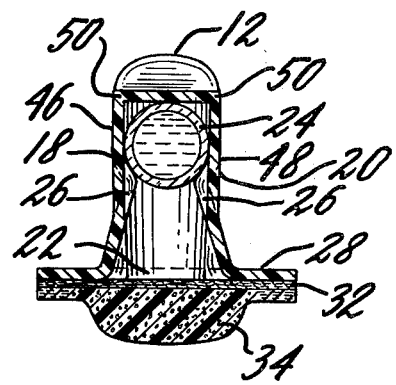
FIG. 2 is a transverse sectional view taken along the line 2—2 in FIG. 1.

With reference now to FIGS. 1 and 2, there is depicted therein a first embodiment of the present invention. As will be noted, the dispensing unit comprises a shaped body structure 10 which includes a top wall 12 a pair of end walls 14 and 16 and a pair of side walls 18 and 20 which side and end walls terminate at a bottom opening 22 to define a housing in which is received a fluid-filled ampoule 24, the side walls 18 and 20 of the housing being provided with inwardly directed projections 26 which are paired at opposite ends of the housing to form a cradle for reception of the ampoule. Furthermore, there is provided at the bottom of the housing, a flange 28 formed integral with the bottom of the side and end walls and which flange fully encircles the bottom opening 22. Secured in sealed connection with the flange member 28 at the underside thereof is a porous pad member shown generally at 30 and which in preferred form is comprised as a plural ply element, there being a first or non-woven material layer 32 such as a non-woven nylon scrim or a cotton or cotton-based material which is disposed immediate the flange, and below which is a second ply of a sponge layer 34 of a reticulated open-celled foam material. For the layer 32, as indicated, a wide range of non-woven materials can be employed, a particularly satisfactory material being "WEBRIL" ® manufactured by Kendall Mills Company. Sponge layer 34 conveniently can be provided as an expanded polyurethane foam. For connecting the porous pad member to the flange 28, various means can be employed. Thus, the pad member could be solvent or flame bonded to the flange or if the porous pad member and housing are of heat sealably compatible materials, they can be secured together by heat sealing of the same.

The gauze layer 32 of porous pad member 30 can be and desirably is, laminated to layer 34 either by solvent effected lamination or flame lamination of the two.

Figure 3:
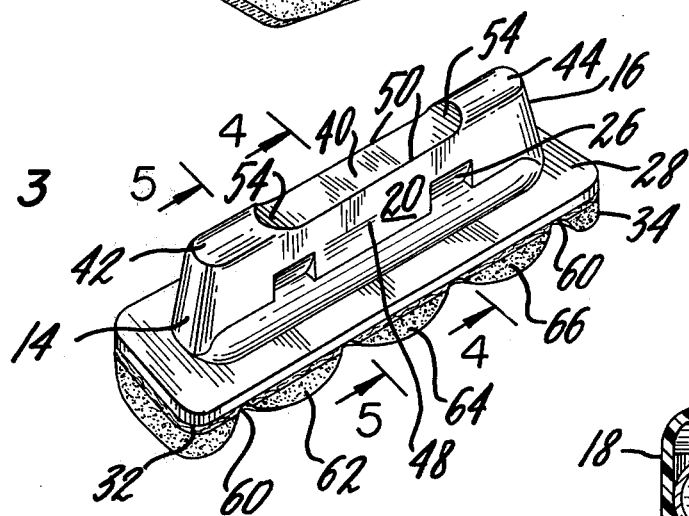
FIG. 3 is a perspective view of a further embodiment of dispensing unit of the present invention in which the porous pad member is provided with dimpling along the longitudinal margins thereof to produce a plurality of discrete sponge or pad segments therein.
Figure 5:
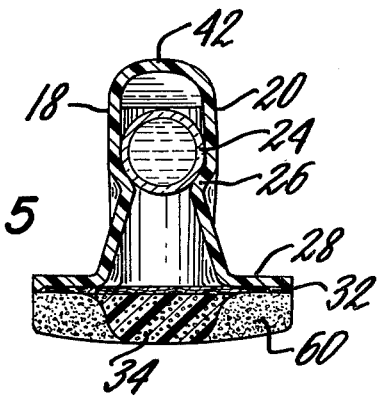
FIGS. 4 and 5 are vertical sectional views as taken along the respective cutting lines 4—4 and 5—5 in FIG. 3.
Figure 6:
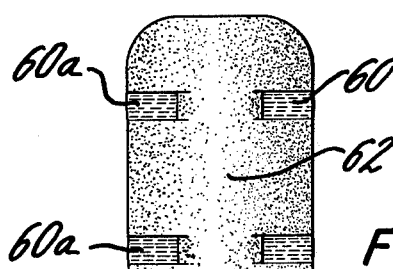
FIG. 6 is a bottom view of the fluid dispensing unit depicted in FIG. 3.
Figure 6:
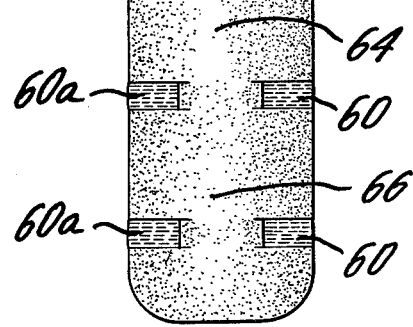
Figure 4:
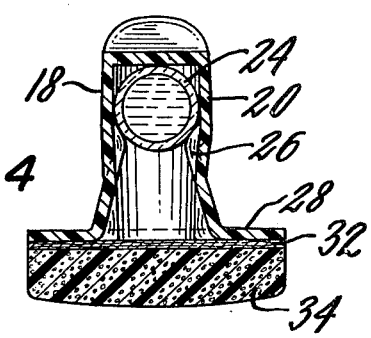

Housing or body structure 10 which conveniently and desirably is provided of high impact styrene material, i.e., a styrene material to which rubber has been added, has the structural rigidity thereof enhanced by the formation in the top wall 12 of a central planar segment 40 which is stepped down relative to the terminal segments 42 and 44 of the top wall, with the central segment 40 merging at its sides with substantially right angularly disposed generally planar portions 46 and 48 of said housing side walls 18 and 20 respectively, to define an inverted housing channel structure of enhanced rigidity embracing the ampoule. The central segment 40 and the right angularly disposed segments 46 and 48 intersect at sharp corner juncture as at 50 to thus provide fulcrum points whereby when squeezing pressure is applied to the side walls, movement thereof is limited to a pivoting of each such wall toward the other about the respective fulcrum points. In this manner, the top wall central segment 40 undergoes no distortion or upward bulging as can occur in the device disclosed in the above-mentioned application with consequent result that the side walls upon application of squeezing pressure are susceptible to excessive movement toward each other and possible puncture of the side walls and injury of the user's fingers from ampoule glass particles. As will be noted in FIG. 3, the top wall central segment 40 merges with the terminal segments 42 and 44 in a transitional course along an upwardly curving path as at 54.

In use, the user grasps the housing between the thumb and index finger and applies squeezing pressure with such fingers, the fingers engaging the corner junctures 50 and as fulcrums so that the tip ends of the fingers are employed to provide levering pressure against the side wall straight segments 46 and 48 to effect crushing of the ampoule, such occurring however with sufficient finger control by the user to immediately release pressure upon the fracturing of the ampoule and without having applied such excessive pressure as would cause any total inward movement of the side wall structure.

FIGS. 3–6 depict a further improvement in the dispensing unit of the present invention which unit is in all respects like that already described except that the porous pad member 30 has its gauze material layer 32 bonded to the underside of flange 28 in suitable manner as by solvent bonding, flame bonding or other means for establishing a full encircling connection between it and the flange. Additionally, the sponge layer 34 is heat sealed along with corresponding portions of the gauze layer 32 to the underside of the flange 28 of the housing at spaced locations along the longitudinal margins of the pad member. The heat sealings or dimples 60 which are formed in the porous pad member are at one margin paired with those at the other margin so that each pair of dimples 60, 60a with an adjacent pair define discrete pad segments 62, 64 and 66 which stand out from the bottom of the unit in the manner best seen in FIG. 3 to provide a plurality of separate or discrete sponge sections. The heat seal or dimpling is effected coextensibly with the width of the flange 28 and results in enhancement of the saturation of the full broad surface of the porous pad with fluid following breaking of the ampoule. Additionally, the presence of relatively thick portions of sponge material at the side margins reduces the likelihood of irritating the skin of a user where, for example, the dispensing unit is used for applying medicament or cleansing a wound region.

It will thus be seen that the improved fluid dispensing unit of the present invention is highly suited for a multitude of uses where it is desired to dispense a fluid for a particular purpose such as a medicament, cosmetic, polish, antiseptic, or detergent composition and the like. Furthermore, the unit can be manufactured readily and inexpensively using mass production techniques and in particular can be manufactured with great facility with the apparatus and method described in the above-identified abandoned patent application.

While there is disclosed but several embodiments of improvements of the dispensing unit of the present invention, it is possible to produce still other embodiments without departing from the scope of the inventive concept herein disclosed, and accordingly, it should be understood that all matter contained in the above description and in the accompanying drawings should be interpreted as illustrative and not in a limiting sense.

What is claimed is:

1. In a fluid dispensing unit comprising a shaped body structure having side walls, end walls, a top wall and a bottom opening defining a housing, there being a flange formed integral with the bottom of said side and end walls and encircling said opening, a porous pad member covering said opening and in sealed connection with said flange member, and an elongated frangible ampoule containing fluid carried in said housing and extending longitudinally thereof between said side walls, the body structure being of sufficiently flexible material to permit digitally applied squeezing together of said side walls to fracture said ampoule and release the fluid therein for transmission of same to and through said porous pad member, the improvement wherein said housing top wall has a central planar segment thereof stepped down relative to terminal segments of said top wall and merging with substantially right angularly disposed generally planar portions of said housing side walls to define an inverted housing channel structure of enhanced rigidity embracing said ampoule, the central segment of said top wall and right angularly disposed portions of said side walls intersecting at sharp corner juncture to provide fulcrum points whereby during the squeezing together of said side walls for fracturing said ampoule, upward bulging of said central segment is prevented, and side wall movement at least along lengths thereof coextensive with said top wall central segment is limited to pivoting of each toward the other about the respective fulcrum point.

2. The fluid dispensing unit of claim 1 wherein the structure of said flange is disposed in a single plane, and the central planar segment of said top wall is parallel with said single plane.

3. The fluid dispensing unit of claim 1 wherein the central planar segment of said top wall has merging transition with the top wall terminal segments along an upwardly curving course.

4. The fluid dispensing unit of claim 1 wherein said porous pad member is a plural ply element including a gauze-like sheet layer and sponge layer of a reticulated open cell foam material bonded to said sheet layer, said sheet layer being immediate said flange.

5. The fluid dispensing unit of claim 4 wherein said sheet layer is a non-woven fabric.

6. The fluid dispensing device of claim 4 wherein said sheet layer and sponge layer are solvent bonded one to the other.

7. The fluid dispensing device of claim 4 wherein said sheet layer and sponge layer are flame laminated one to the other.

8. The fluid dispensing unit of claim 1 wherein said porous pad member and said housing are of heat sealable materials, and said pad member is heat sealed to said flange along the full encircling course thereof.

9. The fluid dispensing unit of claim 1 wherein said porous pad member is bonded to said flange along the full encircling course thereof.

* * * * *